US011534287B2

(12) United States Patent
Persson

(10) Patent No.: US 11,534,287 B2
(45) Date of Patent: Dec. 27, 2022

(54) IMPLANT FOR SOFT TISSUE RECONSTRUCTION

(71) Applicant: International Life Sciences, LLC, Marietta, GA (US)

(72) Inventor: Anders Persson, Gothenburg (SE)

(73) Assignee: INTERNATIONAL LIFE SCIENCES LLC, Marietta, GA (US)

( * ) Notice: Subject to any disclaimer, the term of this patent is extended or adjusted under 35 U.S.C. 154(b) by 1210 days.

(21) Appl. No.: 15/954,376

(22) Filed: Apr. 16, 2018

(65) Prior Publication Data
US 2018/0230628 A1 Aug. 16, 2018

Related U.S. Application Data

(62) Division of application No. 12/504,054, filed on Jul. 16, 2009, now abandoned.

(51) Int. Cl.
*A61F 2/08* (2006.01)
*A61L 27/56* (2006.01)
*A61L 27/16* (2006.01)
*A61L 27/50* (2006.01)
*D04B 21/20* (2006.01)

(52) U.S. Cl.
CPC .............. *A61F 2/08* (2013.01); *A61L 27/56* (2013.01); *A61L 27/16* (2013.01); *A61L 27/50* (2013.01); *A61L 2430/34* (2013.01); *D04B 21/20* (2013.01); *D10B 2509/00* (2013.01)

(58) Field of Classification Search
CPC ... A61F 2/08; A61F 2002/0894; D04B 21/20; D04B 21/202
See application file for complete search history.

(56) References Cited

U.S. PATENT DOCUMENTS 6,547,820 B1    4/2003  Staudenmeier ............... 623/1.49
2008/0188933 A1* 8/2008  Koob .................... C07K 14/78
                                                    623/13.12

FOREIGN PATENT DOCUMENTS

WO    WO 01/32229        5/2001    ............. A61L 27/18
WO    WO 09/93954        7/2009    ............... A61F 2/02
WO    WO-2009093954 A1 * 7/2009    ......... A61F 2/30756

OTHER PUBLICATIONS

EP Examination Report issued in related foreign application, EP 10800107.4, pp. 1-8, (dated Nov. 25, 2020).
Richard H. Gelberman et al., "The Effect of Gap Formation at the Repair Site on the Strength and Excursion of Intrasynovial Flexor Tendons", The Journal of Bone and Joint Surgery, Jul. 1999, pp. 975-982, vol. 81-A, No. 7, The Journal of Bone and Joint Surgery, Incorporated.

(Continued)

*Primary Examiner* — William H Matthews
(74) *Attorney, Agent, or Firm* — Michael A. Bertelson, Esq.; Kilpatrick Townsend & Stockton LLP

(57) ABSTRACT

Method of making a musculoskeletal tissue reconstruction implant by warp knitting an implant of a biodegradable polymeric material to form a porous matrix or scaffold having a tensile stiffness at least by 50% lower than the tensile stiffness of the musculoskeletal tissue the implant is configured to reconstruct.

15 Claims, 6 Drawing Sheets

(56) References Cited

OTHER PUBLICATIONS

K.M. Hirpara et al., "A biomechanical analysis of multistrand repairs with the Silfverskiold peripheral cross-stitch", The Journal of Bone and Joint Surgery, Oct. 2007, pp. 1396-1401, vol. 89-B, No. 10, British Editorial Society of Bone and Joint Surgery.
Cara Matthew et al., "A Quantitative Ultrastructural Study of Collagen Fibril Formation in the Healing Extensor Digitorum Longue Tendon of the Rat", The Journal of Hand Surgery, Oct. 1987, pp. 313-320, vol. 12-B, No. 3.
Toshimitsu Momose et al., "Suture techniques with high breaking strength and low gliding resistance", Acta Orthop Scand, 2001, pp. 635-641, vol. 72, No. 6, Taylor & Francis.
D. Palmes et al., "Achilles tendon healing: Long-term biomechanical effects of postoperative mobilization and immobilization in a new mouse model", Journal of Orthopaedic Research, 2002, pp. 939-946, vol. 20, Elsevier Science Ltd.
James H.-C. Wang, "Mechanobiology of tendon", Journal of Biomechanics, 2006, pp. 1563-1582, vol. 39, Elsevier Ltd.
Andreas Weiler et al., "Biomechanical Properties and Vascularity of an Anterior Cruciate Ligament Graft Can Be Predicted by Contrast-Enhanced Magnetic Resonance Imaging", American Journal of Sports Medicine, 2001, pp. 751-761, vol. 29, No. 6, American Orthopaedic Society of Sports Medicine.
EP Extended Search Report and Opinion, EP 10800107.4, pp. 1-10, (dated Dec. 14, 2017).

* cited by examiner

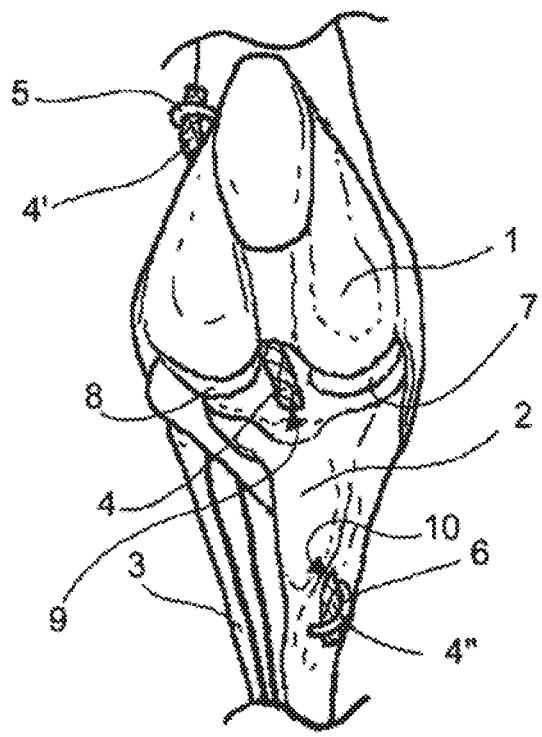
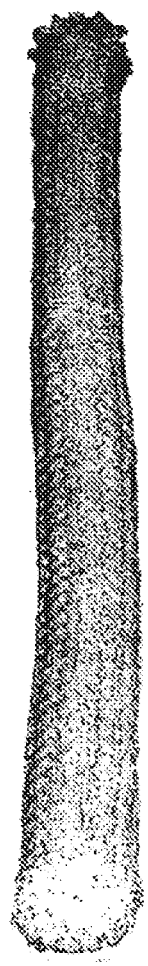
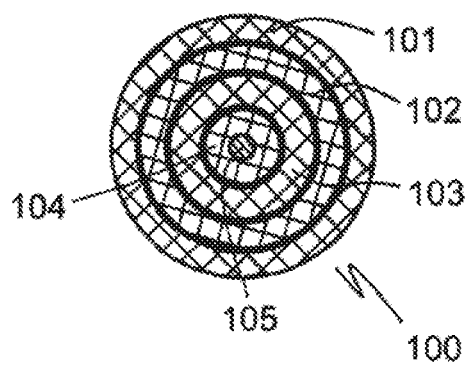
Fig. 8a   Fig. 7
Fig. 8b

IMPLANT FOR SOFT TISSUE RECONSTRUCTION

CROSS-REFERENCE TO RELATED APPLICATIONS

This application is a divisional of U.S. patent application Ser. No. 12/504,054, filed Jul. 16, 2009 and incorporated by reference herein.

BACKGROUND OF THE INVENTION

The present invention relates to a surgical implant or graft for soft issue reconstruction.

Surgical treatment of injury to soft tissues of the muscular-skeletal system of mammals caused by trauma, sudden overload, fatigue, sickness or other degenerative medical condition may in some cases benefit from or even require structural support to start healing. An example of such a situation is injuries to structures that do not heal spontaneously such as the intraarticular crucial ligaments. A text book or review paper on sports medicine in general starts out with a phrase stating that " . . . anterior cruciate ligament (ACL) rupture is the most common chronically incapacitating injury . . . " stresses the importance to find a cure for this condition. The golden standard surgical therapy for ACL reconstruction is to put a biological graft where the native ACL used to be. Biological grafts can be either of auto or allogenic origin. Since grafts of allogenic origin poses a risk for disease transmission autograft is preferred instead. However, also autografts have inherent problems such as donor site morbidity. Furthermore, before the angiogenesis of the graft has proceeded far enough to regain proper nutrition the graft goes through a necrotic phase that compromises its mechanical properties (Weiler, A. et al., *Biomechanical properties and vascularity of an anterior cruciate ligament graft can be predicted by contrast-enhanced magnetic resonance imaging. A two-year study of sheep.* Am J Sports Med 2001, 26(6): 751-761). This critical time of about 12 weeks restricts the intensity by which the rehabilitation program can proceed. Overload during this sensitive period can cause permanent elongation of the graft that inevitably ends up in a reconstruction failure. Hence, much effort has been put into development of alternative grafts of biological or synthetic origin.

There is a consensus in both the medical device industry and the scientific community that the stronger a soft tissue reconstruction can be made the better. For instance Wright Medical highlights the superior strength of their augmentation patch "GraftJacket MaxForce Extreme". Also suture branding follows the same path as exemplified by Arthrex Inc. that profiles their FIBERWIRE as: "FIBERWIRE has greater strength than comparable size standard polyester suture. Multiple independent scientific studies document significant increases in strength to failure, stiffness, knot strength and knot slippage with much less elongation" and MAXBRAID by Arthrotek Inc (today Biomet Sports Medicine) is labeled as "the incredible strength suture". Not only should the suture be as strong as possible, there are also numerous scientific papers that aim for the most rigid suture configuration possible (Hirpara, K. M., et al., *A biomechanical analysis of multistrand repairs with the Silfverskiold peripheral cross-stitch.* J Bone Joint Surg Br 2007, 89(10): 1396-1401; Momose, T., et al., *Suture techniques with high breaking strength and low gliding resistance: experiments in the dog flexor digitorum profundus tendon.* Acta Orthop Scand 2001, 72(6): 635-641), e.g. for Achilles tendon repair.

OBJECTS OF THE INVENTION

It is an object of the invention to provide an implant for connective tissue reconstruction that is better adapted to its purpose than implants known in the art.

It is another object of the invention to provide a method of manufacture for such implant.

Further objects of the invention will become apparent from the following summary of the invention, preferred embodiments thereof illustrated in a drawing, and the appended claims.

SUMMARY OF THE INVENTION (Insert Summary)v In this application the terms "implant" and "graft" have the same meaning and designate implants and grafts prior to implantation and as well as in an implanted state. In this application "stiffness" refers to "tensile stiffness". In this application "pre-stretched" and corresponding terms refer to the stretching of an implant or an implant material or portion during implantation and to fixate the implant in a stretched condition. In this application "shrinking", "heat-set" and corresponding terms refers to thermally effected shrinkage of porous implant polymer matrices or scaffolds, in particular of warp knitted synthetic fiber fabrics such as poly(urethane urea) fiber fabrics and implants manufactured from them.

The present invention is based on the insight that an implant for reconstruction of soft tissues of the musculoskeletal apparatus excluding bone and articular cartilage should have properties and be of a design adapted to the natural healing process of connective tissues, in particular dense connective tissues bearing substantial loads such as tendons, fasciae, periostea or ligaments. In this context "adapted to the natural healing process of dense connective tissue" comprises that the implant should, as far as possible, not interfere with the natural healing process of connective tissue. In this application, dense connective tissue to be reconstructed or being in a healing state is termed "target tissue". "Native tissue" signifies connective tissue that has not been damaged. In this application reconstruction of connective tissue comprises reconstruction ab initio as well as reconstruction of damaged connective tissue. The healing process of damaged connective tissue such as a damaged tendon, fascia, periosteum, ligament or muscle starts by formation of disorganized scar tissue. This scar tissue, the physical properties of which do substantially differ from those of the corresponding uncompromised tissue, is mechanically significantly weaker and less stiff. Hence, loads cause larger deformations of a healing soft tissue than of the corresponding uncompromised native tissue. As the healing process proceeds matrix producing cells form functional tissues. During the healing process the regenerating target tissue matures progressively and increasingly resembles the native tissue (Matthew, C., M. J. Moore, and L. Campbell, *A quantitative ultrastructural study of collagen fibril formation in the healing extensor digitorum longus tendon of the rat.* J Hand Surg [Br] 1987, 12(3): 313-320). It is of paramount importance that a healing target tissue be offered adequate mechanical stimuli to make it form functional tissue resembling native tissue. The implant of the invention and the material(s) of which it is made is preferably biocompatible and biodegradable; if biodegradable, its degradation rate is slow, such as that it offers substantial mechanical support after one year from implantation and even two years or more from implantation. "Substantial mechanical support" is a mechanical support of from 20% to 50% or more of the mechanical support at the time of implantation. By selection of a proper material the biodegradation rate can be advantageously adapted to the expected healing rate of the tissue to be reconstructed.

According to the present invention is disclosed an implant for reconstructing soft tissues of the musculo-skeletal apparatus, in particular tendon, fascia, periosteum, ligament, muscle but excluding bone and articular cartilage having an initial tensile stiffness that is significantly lower than that of the tissue to be reconstructed. In this application "initial stiffness" is the tensile stiffness at the time of implantation. The implant of the invention has a porosity and texture capable of accommodating matrix producing cells to form a functional tissue. Furthermore, the implant material of the invention is capable of resisting long term stress relaxation and creep thereby avoiding plastic deformation of the implant. Stress relaxation that rapidly levels off (within, for instance, one minute) is acceptable while plastic deformation (elongation) is not. Plastic deformation or creep ruins the implant's ability to template the healing tissue to its desired dimensions ensuring correct kinematics. The ability to support an applied load with an initial stress relaxation that rapidly levels off asymptotically to a finite value is beneficial to the implant for two reasons. Firstly, the residual load generated from the pre-stretch procedure can reapproximate retracted tissues, a clinical condition often seen, for instance, in tendon injuries such as rotator cuff tears or in avulsion injuries. Secondly, the residual pre-stretch force of a pre-stretched implant used in joint surgery provides active joint stabilization. This kind of active joint stabilization is important for intra-articular ligament reconstruction according to the invention. The nature of stress relaxation of fabrics is two-fold. There are contributions both from the textile design and from the material itself. Depending on fiber interlocking the fibers slide in respect of each other; with an elastic material this sliding will be gradual and appear as a rapid stress relaxation. The material's resistance to stress relaxation is strongly dependent on inherent limitation of molecular mobility by cross-links that may be chemical or physical. Chemical cross-links are found in e.g. rubbers while physical cross-links of permanent character are found in e.g. poly (urethane urea). The limited molecular mobility also offers the ability to orient the molecular network by simply stretching the implant and thereby modulate its stiffness. The molecules orient along the direction of the applied pre-stretch. Thereby the implant is stiffened in the pre-stretch direction.

A property of paramount importance of the implant of the invention is that it should be made of a material or comprise a material of a relaxation behaviour such that its relaxation upon tensioning quickly approaches asymptotically a finite value. A preferred material of this kind is polyurethane, in particular poly (urethane urea).

The textile material of the invention is preferably a warp-knitted fabric. By this textile design the implant can be made particularly resistant to frying. Resistance to frying is a crucial factor in fixation of an implant to connective tissue when penetrating fixation elements such as sutures are being utilized. Except for articular cartilage, the soft tissues of the musculo-skeletal apparatus addressed by this implant may be connected to bone at one or both implant ends. For the implant to transfer load to and from tissue it is essential that it can be securely and conveniently attached to the tissue. Attachment to soft tissue is normally accomplished by suturing whereas fixation to bone is a more delicate task. Fixation to bone hinders movement at the bone-implant interface. Penetrating, holding or squeezing fixation elements may be considered, for instance, for bone-implant attachment. Examples of fixation elements for these kinds of fixation, i.e. penetrating, holding or squeezing fixation, are sutures and screws, button with a sling such as ENDOBUTTON™ and ACL/PCL interference screws that both may be metallic or bioresorbable.

The design of the implant governs how it can be applied and interfaced with host tissue. A square or rectangular fabric that permits bed side trimming in all directions enables adaptation to optimize fitting and attachment to its host structure by penetrating fixation devices. For a design with a high aspect ratio, such as a substantially linear implant in form of a rope or thin strip, intended to transfer a load in a direction of the implant's longitudinal extension, the implant is normally attached near its both ends by penetrating or squeezing fixation elements. In this application "aspect ratio" denotes a length to width ratio. The ability of an implant to transfer a load across the implant-fixation element interface depends on its stress distribution properties. Extreme stress concentrations need to be leveled or avoided. One fixation mode that distributes stresses efficiently is by a linear implant being folded over a holding fixation element, such as an integrated fibrous sling over a button element, a cross-pin or directly over a button or pin. Clinically utilized brands comprising such elements include ENDOBUTTON™, RETROBUTTON™, TOGGLELOC™, CROSSPIN™ and ENDOBUTTON DIRECT™.

As mentioned in the foregoing healing of native tissue by a target tissue is a slow process, extending over months and even years. In view of this the implant of the invention shall be made of a biocompatible material with a corresponding in vivo endurance, in particular one that ensures that at least half of the stiffness persists for at least one year, preferably at least two years upon implantation. Furthermore, it is preferred that the implant material of the invention be more adapted to deformation than the target tissue so as to ensure matrix continuity even if the healing target tissue is overstretched, causing partial or total laceration. In such case the healing of a damaged target tissue will restart and continue to be supported by the implant without the need for repeated surgery.

The present invention additionally discloses an implant made of the material of the invention manufactured into a porous matrix, a template, an added synthetic extracellular matrix, but most often referred to as a scaffold. The implant has a tensile stiffness significantly lower than that of the native tissue it is intended to reconstruct, for instance lower by at least 50% or at least 80% or 8% and even as much as 90% or more. The material of the invention has elastomeric characteristics, which ensures that the implant can be deformed without permanent elongation. The implant may be manufactured by processes with inherent ability to accomplish porosity such as foaming, porogen extraction from molded block, textile confection or non-woven structures made out of fibers. It is also possible to manufacture it from combinations of these processes such as a porous matrix reinforced by fibers or a fabric.

The invention will now be explained in greater detail by reference to preferred embodiments thereof illustrated in a rough drawing.

BRIEF DESCRIPTION OF THE DRAWINGS

FIG. 1A Top view of a transverse section of a warp knitted poly(urethane urea) fiber fabric;

FIG. 3B Tensile force/elongation diagram corresponding to the tensile force/time diagram of FIG. 3a;

FIG. 7 Anterior (craniate) cruciate ligament implant of the invention according to FIG. 6a, 6b applied through bone tunnels in the femur and the tibia with extra-articular staple fixation, in a posterial view;

FIGS. 8a-b Filled cylinder implant manufactured from four knitted poly (urethane urea) tubes of different diameter, consecutively heat-set on steel core wire, in a perspective view (8a); in a transverse, enlarged sectional view (8b) prior to removing the steel core wire;

DETAILED DESCRIPTION OF THE PREFERRED EMBODIMENTS

Example 1

Figure 1A:
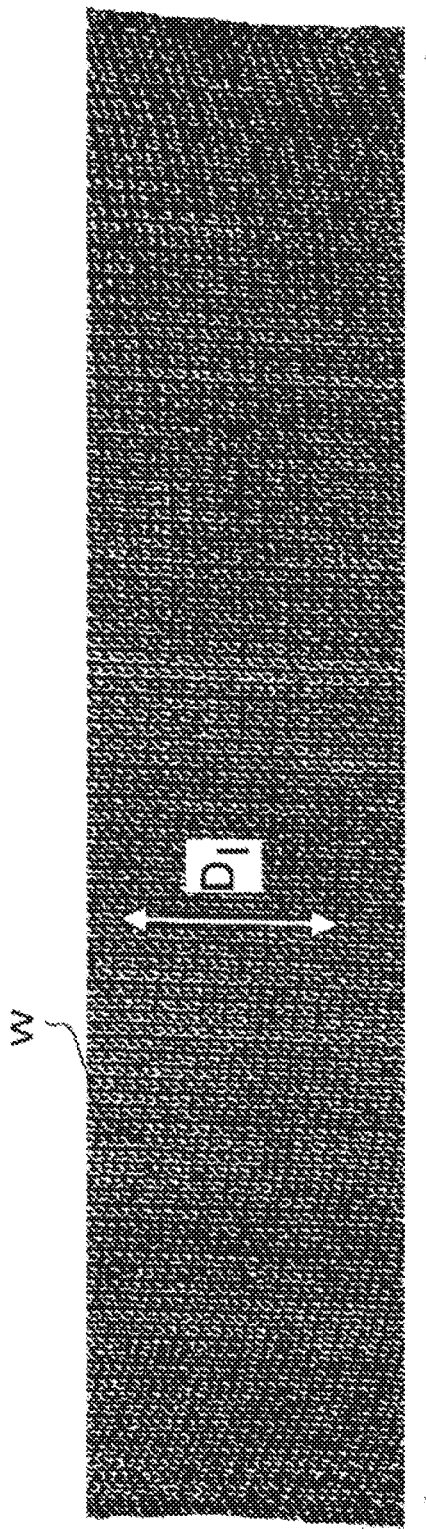
Figure 1B:
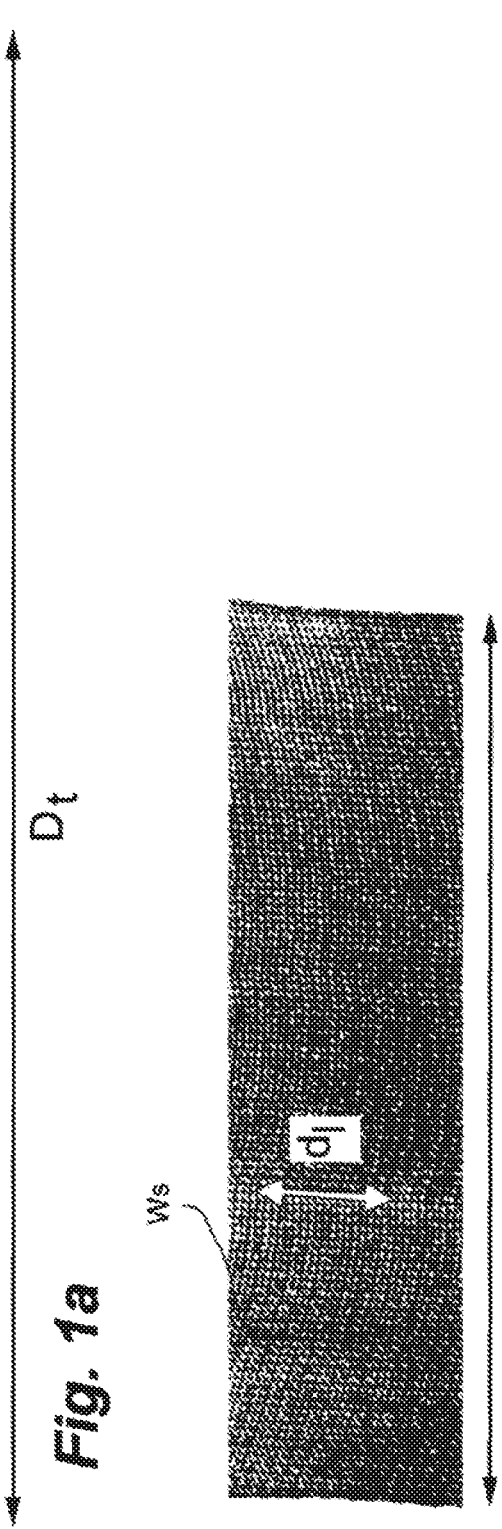
FIG. 1B The transverse section of the fabric of FIG. 1a, heat-set (thermally crimped) and in the same view.
Figure 2:
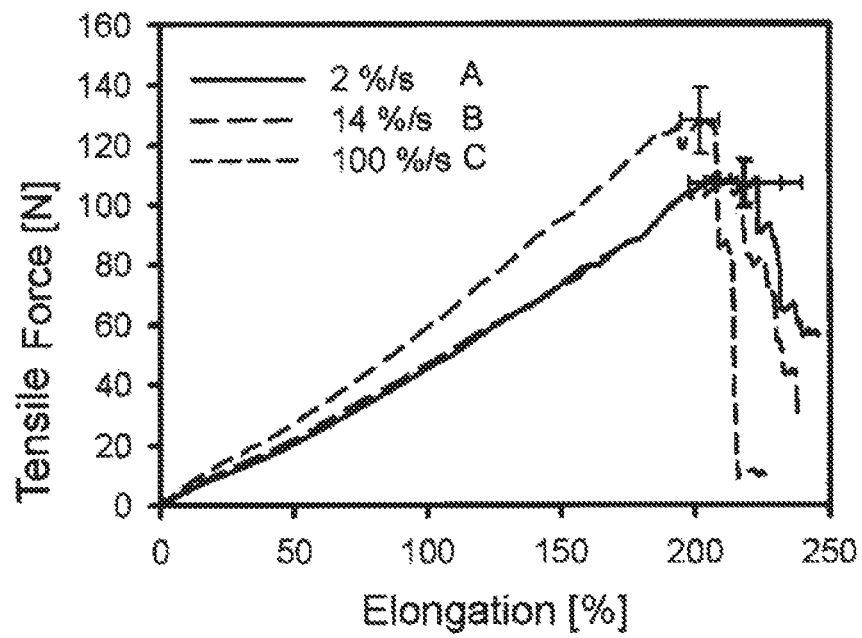
FIG. 2 Tensile force/elongation diagram illustrating of a cut-out strip of the fabric of FIG. 1b, at three elongation rates.

Shrunk knitted poly (urethane urea) ribbon. Yarn: 13 Tex poly(urethane urea) (ARTELON®, Artimplant AB, Goteborg, Sweden). Equipment: Comez DNB/EL-800 (Comez s.p.A., Cilavegna, Italy) double needle bed crochet machine, for the production of technical and medical articles. Machine specifications: 15 gauge, 6 weft bars, double needle bed, latch needles. Heat set unit: Comez HSD/800 comprising 2 heat-set cylinders. A plain ribbon W of 14 cm width was knit in the machine (FIG. 1). The ribbon W was shrunk in the heat set unit at 130° C. to produce a shrunk ribbon Ws at a thickness of 0.8 mm (FIG. 1).

Process parameters: Knitting speed: 26 cm/min; heat set unit speed: 14 cm/min; shrinkage along warp: about 45% (cf D" width of ribbon W and d" width of ribbon Ws); shrinkage across warp: about 45% (cf Dt, 20 loops, and dr. 20 loops). Warp thickness is slightly increased by shrinking. The warp knitting pattern is shown in Table 1. It is a sequence of four steps with 12 loops/cm.

TABLE 1

Warp knitting pattern of tricot ribbon

| Loop row | Binding device movement | | | | | | Loops/cm | Alimentation device setting (warp feed) | | | |
|---|---|---|---|---|---|---|---|---|---|---|---|
| | 2 | | 4 | | 5 | | | | | | |
| 1 | 2 | 2 | 3 | 3 | 2 | 2 | 12.00 | 1490 | 2610 | 1790 | 1450 |
| 2 | 2 | 1 | 2 | 1 | 2 | 3 | 12.00 | 1490 | 2610 | 1790 | 1450 |
| 3 | 1 | 1 | 3 | 3 | 2 | 2 | 12.00 | 1490 | 2610 | 1790 | 1450 |
| 4 | 1 | 2 | 4 | 5 | 2 | 1 | 12.00 | 1490 | 2610 | 1790 | 1450 |
| 5 | 2 | 2 | 3 | 3 | 2 | 2 | 12.00 | 1490 | 2610 | 1790 | 1450 |
| 6 | 2 | 1 | 2 | 1 | 2 | 3 | 12.00 | 1490 | 2610 | 1790 | 1450 |
| 7 | 1 | 1 | 3 | 3 | 2 | 2 | 12.00 | 1490 | 2610 | 1790 | 1450 |
| 8 | 1 | 2 | 4 | 5 | 2 | 1 | 12.00 | 1490 | 2610 | 1790 | 1450 |

Example 2

Tensile force v. elongation of strip samples of the fabric of Example 1. Ten millimeter wide strip samples were cut from the crimped knitted fabric As of Example 1. The elongation of three samples A, B, C at physiological elongation rates of 2%/s (A), 14%/s (B), and 100%/s (C), gauge length of 20 mm, and physiological conditions, was recorded. Physiological conditions imply pH-buffered saline at 37° C. The curves for samples A and B were practically identical up 200% elongation. The samples burst at an elongation of about 220% and 230%, respectively. In contrast, sample C required an about 20% higher force for a given elongation and burst already at an elongation of about 210%.

Example 3

Figure 3A:
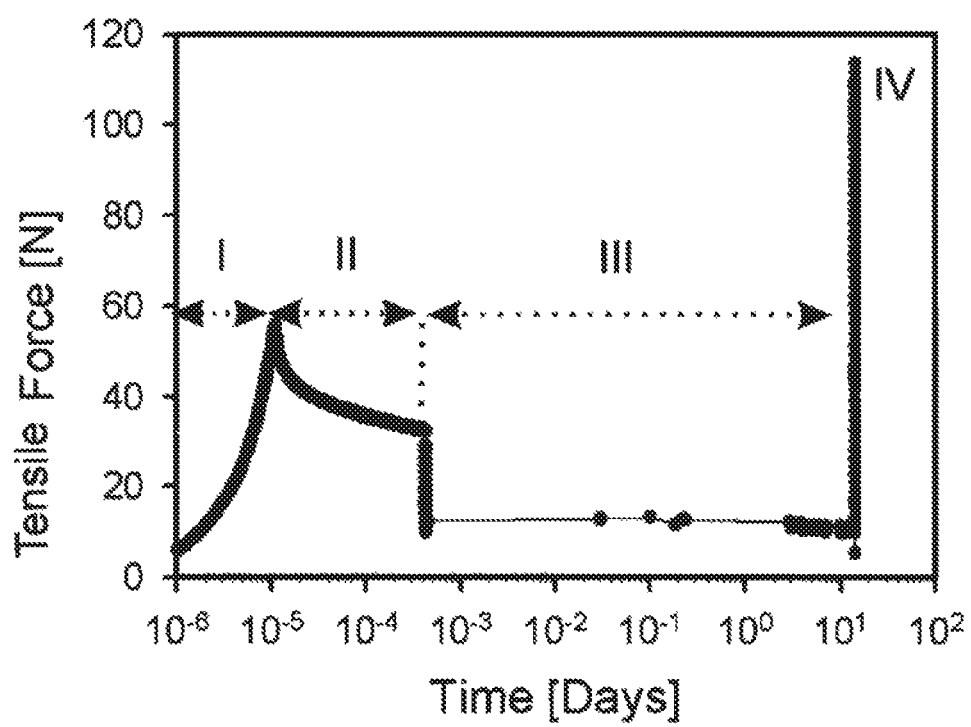
FIG. 3A Tensile force/time diagram of stretching a cut-out strip of the fabric of FIG. 1b in three steps.
Figure 3B:
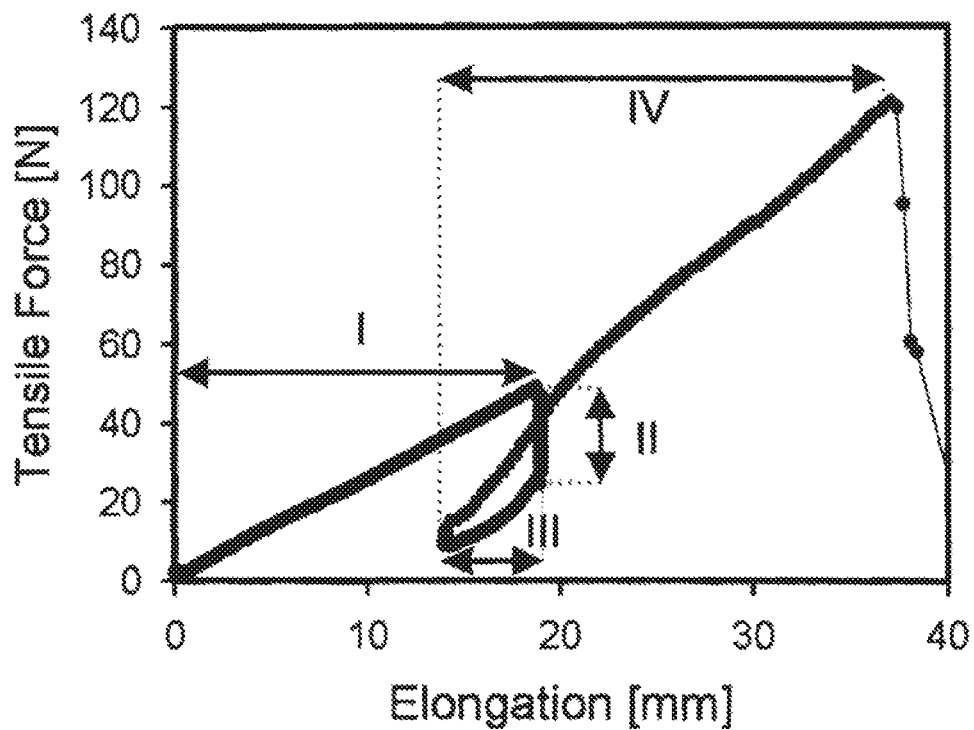

Tensile force v. time of a sample of the fabric of Example 1. A 10 mm wide cut-out strip sample of the crimped knitted fabric As of Example 1, gauge length 20 mm, was stretched in a first step I to an elongation of 95% at about 55 N, elongation rate of 100%/s (FIG. 3a). Within a minute the force needed to keep the sample at that elongation dropped to about 35 N, step II. In a following step III the pre-stretched sample was kept at a reduced elongation of 70% for two weeks, during which period the free sample length remained constant. A bursting test at an elongation rate of 100%/s, step IV, concluded the experiment. The elongation of the sample during the stretching procedure is shown in FIG. 3b.

Example 4

Figure 4:
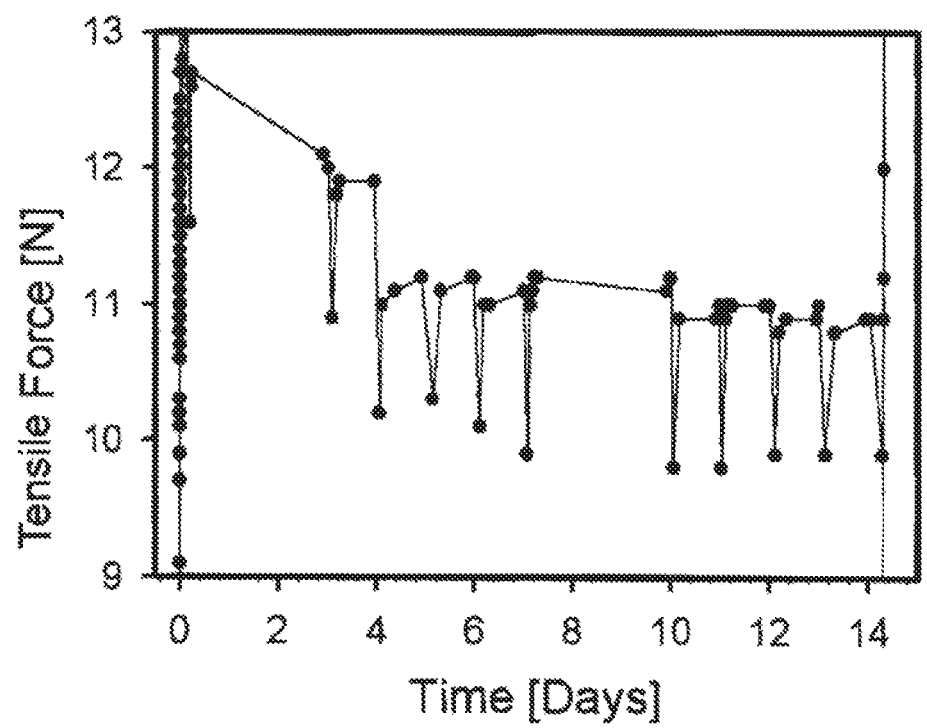
FIG. 4 Tensile force/time diagram of stretching a cut-out strip of the fabric of FIG. 1b to 70% elongation, followed by superimposing for two weeks a daily (weekdays: Monday to Friday) 10% elongation harmonic at 1 Hz for one hour.

Tensile force v. time of a pre-stretched sample of the fabric of Example 1 under physiological load. The diagram of FIG. 4 illustrates how the sample of Example 3 endures daily exercise. Experimental conditions were those of Example 3 except for superposition of a 10% elongation harmonic at 1 Hz in step III, one hour daily during two periods of five days each separated by two days during which no such superposition was carried out.

Example 5

Figure 5:
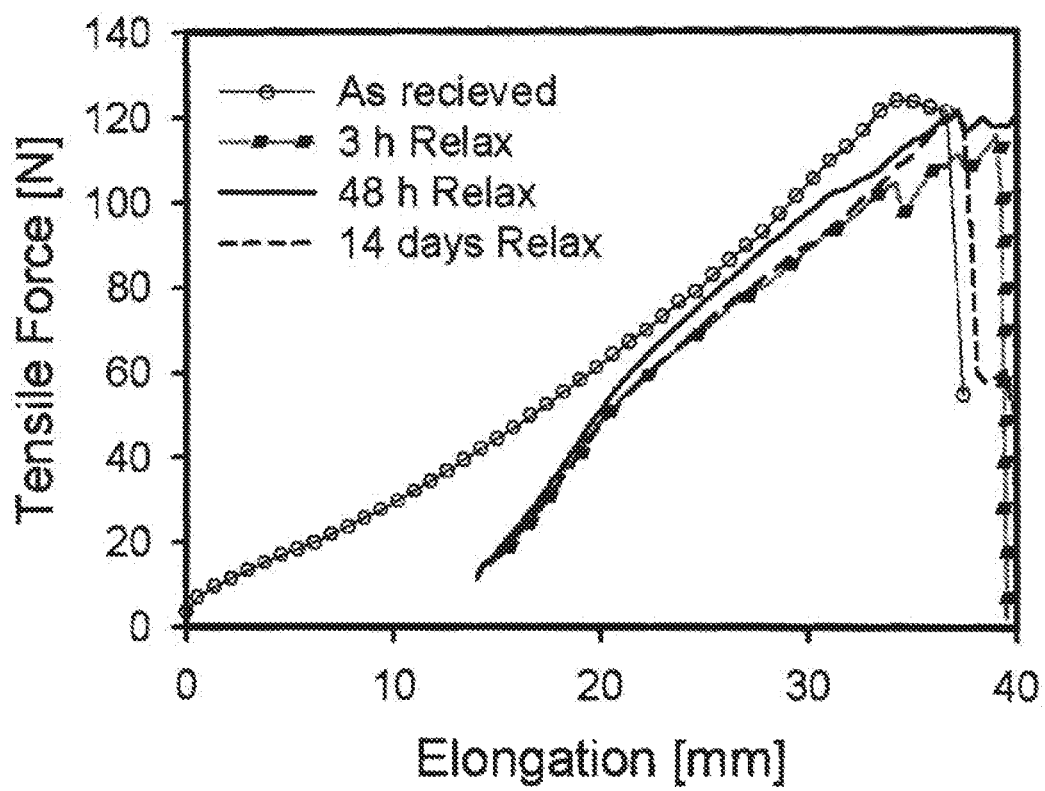
FIG. 5 Tensile force/elongation diagram of cut-out strips of the fabric of FIG. 1b stretched to 70% elongation and relaxation of 3 hours, 48 hours, and 14 days at this elongation, in comparison with a non-prestretched strip.

Tensile force v. elongation in dependence of relaxation time. Ten millimeter wide cut-out strip samples of crimped knitted fabric, as the fabric of Example 1, were pre-tensioned and allowed to relax at an elongation of 70% for 3 h (D), 48 h (E), and 14 days (F). Their elongation behavior at an elongation rate of 100% was nearly identical (FIG. 5) and differed substantially from the elongation behavior of a non-pre-stretched sample (G).

Example 6

Figure 6A:
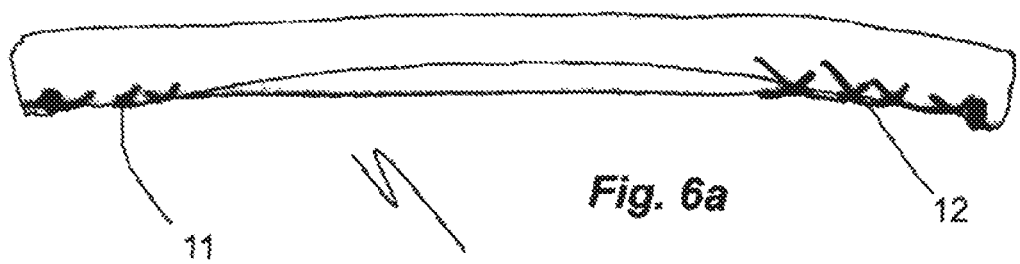
FIGS. 6a-c Wrapped-up cut-out strips of the fabric of FIG. 1b; 6 mm diameter, 6a, side view, 6b, transverse section, enlarged; four mm diameter, 6c, side view.
Figure 6B:
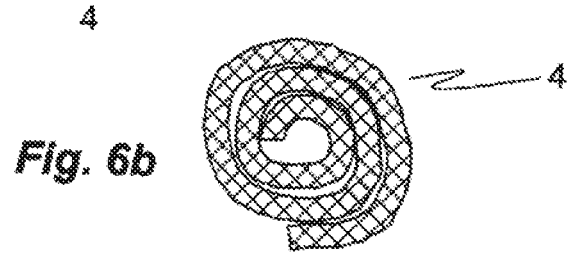

A 90 mm×33 mm strip was cut from the crimped knitted fabric As of Example 1. The strip was wrapped up to a 90 mm long, 6 mm diameter implant 4 (FIGS. 6a, 6b). The implant 4 had a porosity of about 50%. It was intra-synovially implanted as a temporary prosthesis 4 into a stifle joint 1, 2 of mid- and large size dogs (FIG. 7). The prosthesis 4 provided essential stifle joint 1, 2 stability while acting as a scaffold to recover the cranial cruciate ligament, CCL. The implant 4 was applied through transcortical femur 1 tunnels and tibia 2 tunnels (intra-articular opening at 9, lateral opening at 10) with intra-synovial tunnel openings located at the respective center of the native CCL foot prints (bony ligament attachment sites). By metal staples 5, 6 the implant 4 was extra-articularly fixated at the femur 1 at its upper 4' and in the tibia 2 at its lower 4" terminal sections protruding cranially from the femur 1 and the tibia 2 tunnels. Reference signs 3, 7, 8 designate the fibular and the lateral and medial menisci, respectively. The free length of the implant 4 for elongation upon loading was about 80 mm.

Figure 9:
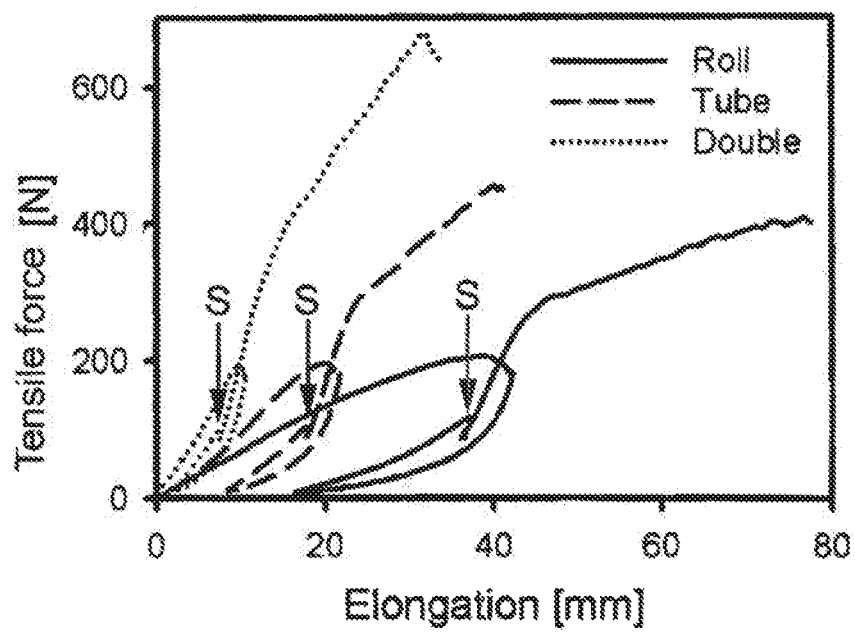
FIG. 9 Tensile force/elongation diagram illustrating the tensile behaviour of the wrapped-up implant of FIG. 6a, 6b, and the filled tube-formed implants of FIGS. 8a, 8b and FIG. 10b.

The mechanical behavior of this implant ("Roll graft") is illustrated in FIG. 9. In an in-vitro experiment the implant was subjected to a pre-stretch procedure followed by a tensile test. The pre-stretch procedure started by a load ramp to 180 N, which was maintained for 20 seconds when the load was reduced to 20 N. At 36 seconds it was ramped to 90 N. The 90 N load was maintained for the remainder of the 100 second pre-stretch procedure. All load ramps were 180 N/s. The deformation achieved at the end of the pre-stretch procedure was maintained for about 1 minute. The tensile behavior of the implant was then tested at a rate of 100% elongation per second. The procedure was conducted under physiological conditions (in 37 degree C. buffer) at a starting free length of 20 mm. The pre-stretch procedure elongated the implant to 57 mm (elongation 37 mm). Tensile testing of the 57 mm long elongated implant gave a stiffness of 26 N/mm. In the clinical situation with staple fixation seen in FIG. 7 the working free implant length was about 80 mm. Hence, the longer implant should be correspondingly more compliant, that is, have a stiffness of 26·57/80=19 N/mm. This is only a fraction of the 148 to 348 N/mm CCL stiffness of dogs reported in literature (Wang, J. H., Mechanobiology of tendon. J Biomech, 2006, 39(9): 1563-1582; Gelberman, R. H. et al., The effect of gap formation at the repair site on the strength and excursion of intrasynovial flexor tendons. An experimental study on the early stages of tendon-healing in dogs. J Bone Joint Surg Am 1999, 81(7): 975-982; Palmes, D. et al., Achilles tendon healing: long-term biomechanical effects of postoperative mobilization and immobilization in a new mouse model. J Orthop Res 2002, 20(5): 939-946). Preliminary data from an ongoing clinical evaluation in 28 dogs indicate that this implant has restored the stifle joint stability of every individual with a follow up time of up to one year.

Example 7

Figure 6C:
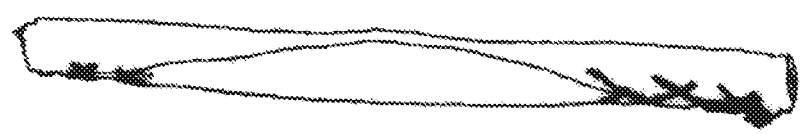

The 4 mm diameter implant illustrated in FIG. 6c was made from a 20 mm wide, 70 mm long cut-out strip of the crimped fabric As of Example 1. With a pre-stretch procedure that caused the same elongation as the implant described in Example 6 the stiffness of the 4 mm implant was scaled accordingly. Its shorter working length (approximately 60 mm) also affects its stiffness: 19·20/33·80/60 N/mm=15 N/mm. Two small dogs were successfully CCL reconstructed with this thinner implant (follow-up period of 6 months).

Example 8

A cylindrical implant 100 (FIGS. 8a, 8b; length 120 mm, diameter 6 mm) was assembled from four tricot tubes 101, 102, 103, 104 of matching diameter inserted into each other. The tubes 101, 102, 103, 104 had been warp knitted from poly(urethane urea) fiber in the machine described in Example 1 where the 6 weft bars were equipped with either, 3 (tube 104), 5 (tube 103), 6 (tube 102) or 7 (tube 101) threads and an equivalent number of needles. The knitting pattern for the tubes is shown in Table 2.

TABLE 2

Warp knitting pattern of tricot tubes.

| Loop row | Binding device movement | | | | | | Loops/ cm | Alimentation device setting (warp feed) | | | |
|---|---|---|---|---|---|---|---|---|---|---|---|
| | 1 | 2 | 4 | 5 | 7 | 8 | | | | | |
| 1 | 2 2 2 2 | 2 1 1 1 | 2 3 2 1 | | | | 12.00 | 1550 | 1650 | 1650 | 1550 |
| 2 | 2 1 2 3 | 2 1 1 1 | 2 2 1 1 | | | | 12.00 | 1550 | 1650 | 1650 | 1550 |
| 3 | 1 1 2 2 | 2 2 1 2 | 2 1 1 2 | | | | 12.00 | 1550 | 1650 | 1650 | 1550 |
| 4 | 1 2 2 1 | 2 2 1 2 | 2 2 2 2 | | | | 12.00 | 1550 | 1650 | 1650 | 1550 |

The assembly of the tubes 101, 102, 103, 104 was carried out as follows. A 1.2 mm diameter steel core wire 105 was inserted into the lumen of the 3-needle tube 104. The tube was thermally crimped by pulling it with the inserted steel core wire through a four mm inner diameter steel tube heated to 150 degrees C. Next, the 3-needle tube 104 crimped on the steel core wire 105 was inserted into the lumen of the 5-needle tube 103 and the crimping process repeated by use of a steel tube heated to 150 degrees C. of correspondingly larger inner diameter. In the same manner, the 6-needle tube 102 and the 7-needle tube 101 were crimped step-wise on the already crimped-on tubes 104, 103. After allowing the completed assembly to cool to room temperature and withdrawing the core 105 the implant blank 100 was transversally cut into a number of 120 mm long cylindrical multi-layer implants. In FIG. 9 the elongation response of the tubular implant 100 ("Tube") of this Example is compared with that of the wrapped-up implant 4 of Example 8 ("Roll"), both attributed to the force controlled pre-stretch procedure described in Example 6. Both the elongation caused by the pre-stretch procedure and the slope of the tensile curves starting at S show that the multi-layer implant 100 is stiffer than the wrapped-up (rolled) implant 4 of Example 6. At otherwise identical experimental conditions the higher stiffness of the multi-layer cylindrical 100 implant provides higher joint stability than the wrapped-up implant 4. Tensile testing of the multi-layer implant 100 consecutive to the pre-stretch procedure showed a stiffness of 37 N/mm. Although this stiffness is higher than that of the implant 4 (26 N/mm) it is still only a fraction of native tissue stiffness.

Example 9

Figure 10A:
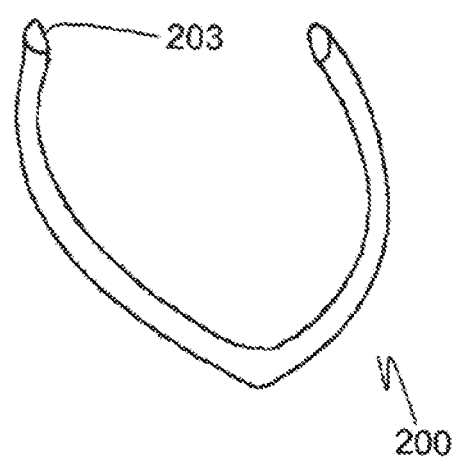
FIG. 10a-b Filled tube implant manufactured from two co-axially disposed tubes of warp-knitted poly(urethane urea) fabric, heat set, cut off and folded into a collar, in a perspective view (10a); implant blank prior to heat setting, in a transverse sectional view (10b), enlarged.
Figure 10B:
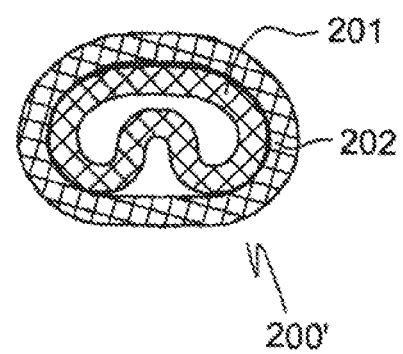

Yet another implant design is shown in FIGS. 10a, 10b. A folded tubular implant blank 200' was manufactured from two 6-needle warp knitted tubes cut to same length manufactured in accordance with the parameters of Table 2, one of them 201 having been inserted in a longitudinally folded state into the other 202 (FIG. 10b). A suitable length of the combination of inner tube 201 and outer tube 202 was wound around a 100 mm diameter stainless steel tube in an about radial plane over an angle of about 335°, clamped at both ends and heat-set in an oven at 120 degrees C. for 20 min, making the assembly 201, 202 to shrink radially so as to form implant 200 having a flattened face 203 where the outer tube 202 had been abutting the stainless steel tube. As seen in FIG. 9 application of the force controlled pre-stretch procedure described in Example 6 caused the implant to elongate by 6.6 mm (stiffness 52 N/mm). The "Double" tensile force/elongation curve of FIG. 9 was obtained with the doubled graft of FIG. 10. Although this implant is stiffer than the pre-stretched implants of the other examples its stiffness is still only a fraction of that of a native CCL.

In another set of experiments at physiological conditions samples of the double tube graft were exposed to a static load for periods of up to seven days. The static load, normally denoted creep load, of about one third of the graft's ultimate load maintained for periods of up to 7 days caused the elongation to increase from 52% 17 sec after loading to 71% after seven days of creep.

Example 10

To decrease or increase the thickness of the implant and the method of manufacture accounted for in Example 8 can be varied to comprise a greater or smaller number of concentric warp knitted tubes in order to decrease or increase the thickness of the implant. Also the number of needles employed to knit the individual tubes will alter the features of the product. Furthermore, restrictions and or loads applied during the heat setting may be utilized to alter the dimensions and mechanical properties of the implant.

Example 11

To increase or decrease the thickness of the implant of FIG. 8 the design and method of manufacture of Example 9 can be applied to smaller or larger assemblies of more or less co-axially disposed warp knitted tubes. Variation of loads on the implant applied during the heat setting can be utilized to alter the dimensions and mechanical properties of the implant.

The invention claimed is:

1. A method for reconstructing anatomic tissue of a musculo-skeletal apparatus, comprising the steps of:
providing a warp knit fabric material implant consisting of a biodegradable single synthetic porous polymeric material having proximal and distal fixation regions and having a tensile stiffness that is at least 50% lower than a tensile stiffness anatomic musculo-skeletal tissue which the implant is reconstructing; and
securing the implant at the proximal and distal fixation regions to the anatomic musculoskeletal tissue.

2. The method of claim 1 wherein the providing step further comprises the step of selecting a porous matrix having a tensile stiffness is at least 80% lower than the tensile stiffness of the anatomic musculo-skeletal tissue the implant is reconstructing.

3. The method of claim 1 wherein the providing step further comprises the step of selecting a porous matrix having a tensile stiffness is at least 90% lower than the tensile stiffness of the anatomic musculo-skeletal tissue the implant is reconstructing.

4. The method of claim 1 wherein the providing step further comprises the step of selecting a porous matrix having a stiffness varying not more than 5% when kept in a stretched condition under constant load for a period extending from 1 hour to 14 days under physiological conditions, wherein the constant elongation is from 0% to 70%.

5. The method of claim 1 wherein the providing step further comprises the step of selecting a porous matrix having an elongation of up to 50% during a time period of from 1 minute to 7 days when exposed to a constant load of 30% of its ultimate load under physiological conditions.

6. The method of claim 1 wherein the providing step further comprises the step of selecting a porous matrix having an elongation of up to 40% during a time period of from 1 minute to 7 days when exposed to a constant load of 30% of its ultimate load under physiological conditions.

7. The method of claim 1 wherein the providing step further comprises the step of selecting a porous matrix consisting of a poly(urethane urea).

8. The method claim 1 wherein the providing step further comprises the step of selecting a porous matrix comprising at least two co-axially positioned tubular knitted fabric implant member.

9. The method claim 1 wherein the providing step further comprises the step of selecting a porous matrix comprising a fabric of an aspect ratio of 20 or more having one or more transverse folds at the proximal and distal regions.

10. The method of claim 9 wherein the step of the implant further comprises the step of affixing the one or more transverse folds at the proximal and distal regions to the anatomical tissue.

11. A method for reconstructing anatomic tissue of a musculo-skeletal apparatus comprising the steps of:
identifying an anatomic tissue for reconstruction, the anatomic tissue comprising a ligament or a tendon, the anatomic tissue for reconstruction having a corresponding native tissue tensile stiffness; and
securing an implant to the anatomic tissue for reconstruction at proximal and distal fixation regions of the implant, the implant comprising a warp knit tissue scaffold comprising a biodegradable synthetic porous polymeric material, the implant having a tensile stiffness that is lower than the native tensile stiffness of the anatomic tissue at the time the implant is secured to the anatomic tissue.

12. The method of claim 11 wherein the implant comprises a stiffness varying not more than 5% when kept in a stretched condition under constant load for a period extending from 1 hour to 14 days under physiological conditions, wherein the constant elongation is from 0% to 70%.

13. The method of claim 11 wherein the implant comprises an elongation of up to 50% during a time period of from 1 minute to 7 days when exposed to a constant load of 30% of its ultimate load under physiological conditions.

14. The method of claim 11 wherein the implant comprises an elongation of up to 40% during a time period of from 1 minute to 7 days when exposed to a constant load of 30% of its ultimate load under physiological conditions.

15. The method of claim 11, wherein the implant comprises a porous matrix comprising a poly(urethane urea).

\* \* \* \* \*